United States Patent
Banner et al.

(10) Patent No.: US 6,571,796 B2
(45) Date of Patent: Jun. 3, 2003

(54) TRACHEAL PRESSURE VENTILATION RESPIRATORY SYSTEM

(75) Inventors: Michael J. Banner, Alachua, FL (US); Paul Bradford Blanch, Alachua, FL (US)

(73) Assignee: University of Florida, Gainesville, FL (US)

( * ) Notice: Subject to any disclaimer, the term of this patent is extended or adjusted under 35 U.S.C. 154(b) by 226 days.

(21) Appl. No.: 09/779,170

(22) Filed: Feb. 8, 2001

(65) Prior Publication Data

US 2002/0104537 A1 Aug. 8, 2002

(51) Int. Cl.$^7$ ............ A61M 16/00; A62B 7/04; F16K 31/26
(52) U.S. Cl. ............ 128/204.26; 128/204.18; 128/204.25; 128/204.16; 128/204.27; 128/205.24; 128/207.15
(58) Field of Search ............ 128/204.21, 207.15, 128/200.24, 200.18, 204.22, 204.23, 207.14, 202.22, 204.18, 204.27, 204.28, 205.24, 207.16, 207.18, 204.25

(56) References Cited

U.S. PATENT DOCUMENTS

| | | | |
|---|---|---|---|
| 3,595,226 A | 7/1971 | Newcombe | 128/142.2 |
| 3,807,396 A | 4/1974 | Fischel | 128/142 |
| 4,520,812 A | 6/1985 | Freitag et al. | 128/204.25 |
| 4,565,194 A | 1/1986 | Weerda et al. | 128/204.23 |
| 4,773,411 A | 9/1988 | Downs | 128/204.18 |
| 4,805,613 A | 2/1989 | Bird | 128/204.25 |
| 4,813,431 A | 3/1989 | Brown | 128/748 |
| 4,905,688 A | 3/1990 | Vicenzi et al. | 128/204.21 |
| 4,957,107 A | 9/1990 | Sipin | 128/204.21 |
| 4,986,268 A | 1/1991 | Tehrani | 128/204.22 |
| 4,990,894 A | 2/1991 | Loescher et al. | 340/573 |
| 5,040,529 A | 8/1991 | Zalkin | 128/204.18 |
| 5,107,831 A | 4/1992 | Halpern et al. | 128/204.26 |
| 5,161,525 A | 11/1992 | Kimm et al. | 128/204.26 |
| 5,303,698 A | 4/1994 | Tobia et al. | 128/204.28 |
| 5,307,795 A | 5/1994 | Whitwam et al. | 128/204.25 |
| 5,315,989 A | 5/1994 | Tobia | 128/204.28 |
| 5,316,009 A | 5/1994 | Yamada | 128/716 |
| 5,331,995 A | 7/1994 | Westfall et al. | 137/8 |
| 5,335,650 A | 8/1994 | Shaffer et al. | 128/200.24 |
| 5,349,946 A | 9/1994 | McComb | 128/203.17 |

(List continued on next page.)

OTHER PUBLICATIONS

09/243,268 dated Feb. 3,1999—co–pending Application to same applicant.

Primary Examiner—Weilun Lo
Assistant Examiner—Darwin Erezo
(74) Attorney, Agent, or Firm—Needle & Rosenberg, PC.

(57) ABSTRACT

Embodiments of the present invention described and shown in the specification and drawings include a respiratory system for automatically and variably controlling the supply of a pressurized breathing gas to a patient via a breathing circuit that is in fluid communication with the lungs of the patient. The respiratory system has a demand valve in fluid communication with a source of pressurized gas. The demand valve is switchable between a open position, in which an inhalation conduit of the breathing circuit is in fluid communication with the source of pressurized gas, and a closed position, in which the inhalation conduit is not in fluid communication with the source of pressurized gas. The demand valve is proportionally moveable between the open and closed positions in response to a pressure within a reference chamber which is in fluid communication with the trachea of the patient. It is emphasized that this abstract is provided to comply with the rules requiring an abstract which will allow a searcher or other reader to quickly ascertain the subject matter of the technical disclosure. It is submitted with the understanding that is will not be used to interpret or limit the scope or meaning of the claims. 37 C.F.R. § 1.72(b).

38 Claims, 7 Drawing Sheets

U.S. PATENT DOCUMENTS

| | | | |
|---|---|---|---|
| 5,390,666 A | 2/1995 | Kimm et al. | 128/204.26 |
| 5,402,796 A | 4/1995 | Packer et al. | 128/719 |
| 5,429,123 A | 7/1995 | Shaffer et al. | 128/204.23 |
| 5,546,935 A | 8/1996 | Champeau | 128/205.23 |
| 5,549,106 A | 8/1996 | Gruenke et al. | 128/204.23 |
| 5,582,163 A | 12/1996 | Bonassa | 128/204.26 |
| 5,598,838 A | 2/1997 | Servidio et al. | 128/204.23 |
| 5,632,270 A | 5/1997 | O'Mahony et al. | 128/204.24 |
| 5,660,171 A | 8/1997 | Kimm et al. | 128/204.23 |
| 5,664,270 A * | 9/1997 | Bell et al. | 5/600 |
| 5,664,563 A | 9/1997 | Schroeder et al. | 128/204.25 |
| 5,692,497 A | 12/1997 | Schnitzer et al. | 128/204.21 |
| 5,752,921 A | 5/1998 | Orr | 600/533 |
| 5,794,615 A | 8/1998 | Estes | 128/204.23 |
| 5,850,835 A * | 12/1998 | Takaki et al. | 128/204.18 |
| 5,884,622 A | 3/1999 | Younes | 128/204.21 |
| 5,906,204 A * | 5/1999 | Beran et al. | 128/207.14 |
| 5,915,381 A | 6/1999 | Nord | 128/204.23 |
| 5,954,050 A | 9/1999 | Christopher | 128/204.23 |
| 6,000,396 A * | 12/1999 | Melker et al. | 128/204.21 |
| 6,095,139 A | 8/2000 | Psaros | 128/204.22 |
| 6,148,816 A | 11/2000 | Heinonen et al. | 128/205.24 |
| 6,390,091 B1 * | 5/2002 | Banner et al. | 128/204.21 |
| 6,450,164 B1 * | 9/2002 | Banner et al. | 128/204.21 |

* cited by examiner

TRACHEAL PRESSURE VENTILATION RESPIRATORY SYSTEM

BACKGROUND OF THE INVENTION

1. Field of the Invention

The present invention relates generally to the field of respiratory assist devices for respiratory care of a patient and, more particularly, to a respiratory system that automatically and variably on demand regulates the supply of a pressurized gas source to provide the appropriate pressure assist to the patient.

2. Background

Mechanical ventilatory support is widely accepted as an effective form of therapy and means for treating patients with respiratory failure. Ventilation is the process of delivering oxygen to and washing carbon dioxide from the alveoli in the lungs. When receiving ventilatory support, the patient becomes part of a complex interactive system which is expected to provide adequate ventilation and promote gas exchange to aid in the stabilization and recovery of the patient.

In those instances which a patient requires mechanical ventilation due to respiratory failure, a wide variety of mechanical ventilators are available. Most modern ventilators, i.e., respiratory systems, allow the clinician to select and use several modes of inhalation either individually or in combination via the ventilator setting controls that are common to the ventilators. These modes can be defined in three broad categories: spontaneous, assisted, or controlled. During spontaneous ventilation without other modes of ventilation, the patient breathes at his own pace, but other interventions may affect other parameters of ventilation including the tidal volume and the baseline pressure, above ambient, within the system. In assisted ventilation, the patient initiates the inhalation by lowering the baseline pressure by varying degrees, and then the ventilator "assists" the patient by completing the breath by the application of positive pressure. During controlled ventilation, the patient is unable to breathe spontaneously or initiate a breath, and is therefore dependent on the ventilator for every breath. During spontaneous or assisted ventilation, the patient is required to "work" (to varying degrees) by using the respiratory muscles in order to breath.

The work of breathing (the work to initiate and sustain a breath) performed by a patient to inhale while intubated and attached to the ventilator may be divided into two major components: physiologic work of breathing (the work of breathing of the patient) and breathing apparatus imposed resistive work of breathing. The breathing apparatus is properly defined as the endotracheal tube, the breathing circuit including an inhalation conduit, an exhalation conduit and a "Y" piece, the gas regulator, such as a ventilator, and may include a humidifier. The work required to spontaneously inhale through the breathing apparatus is the imposed resistive work of breathing ($WOB_i$). The work of breathing can be measured and quantified in Joules/L of ventilation. In the past, techniques have been devised to supply ventilatory therapy to patients for the purpose of improving patient's efforts to breath by decreasing the work of breathing to sustain the breath. It is desirable to reduce the effort expended by the patient since a high work of breathing load can cause further damage to a weakened patient or be beyond the capacity or capability of small or disabled patients.

In conventional respiratory systems, pressure required to inflate the lungs of a patient connected to a life-support mechanical ventilator is typically measured within the breathing circuit from one of three conventional sites: the inspiratory conduit; the expiratory conduit; or the "Y" piece which is connected to both the inspiratory conduit and the expiratory conduit. Conventionally, at the onset of spontaneous inhalation in the pressure support ventilation (PSV) mode, for example, a pressure change is detected in the breathing circuit, the ventilator is triggered "on," and lung inflation is assisted by positive pressure supplied by the ventilator. Pressure is then monitored/controlled from the pressure measuring site to ensure the preselected pressure is achieved, and with some ventilators, the rate of pressure rise over time is controlled based on preselected settings. At a specific pressure, for ventilatory support modes relying on pressure for cycling to the "off" phase, inhalation is terminated.

Inaccurate pressure measurements on the airways and lungs result from using the aforementioned conventional pressure measuring sites. During spontaneous breathing with continuous positive airway pressure (CPAP), for example, significant underestimations of pressure result compared with measuring tracheal pressure at the distal end of an endotracheal tube ($P_T$). This is especially true when using narrow internal diameter endotracheal tubes and when peak spontaneous inspiratory flow demands are high. The narrower the tube and the greater the flow rate demand, the greater the discrepancy or inaccuracy between pressure measured at the "Y" piece and $P_T$.

Due to inherently resistive components within the breathing circuit, in which the endotracheal tube is regarded as being the most significant resistor, the further from the trachea pressure is measured, the smaller the deviations in pressure that occur with CPAP. Small deviations during spontaneous inhalation may lead the clinician to erroneously conclude that the flow rate provided on demand by the ventilator is sufficient and the imposed resistive work of the breathing apparatus is minimal when, in fact, large deviations in pressure at the distal end of the endotracheal tube and a highly resistive workload imposed by the apparatus may be present.

Overestimations in tracheal airway pressure may result during mechanical inflation from the use of the conventional pressure measuring sites. Peak inflation pressure (PIP) generated during mechanical inflation varies directly with total resistance (imposed endotracheal tube resistance and physiologic airways resistance) and inversely with respiratory system compliance ($C_{rs}$). PIP measured at the "Y" piece reflects the series resistance of the endotracheal tube and physiologic airways as well as Crs. Peak pressure measured in the trachea reflects physiologic resistance and Cr, only. Therefore, PIP measured at the "Y" piece may be greater than in the trachea. The narrower the internal diameter of the endotracheal tube and the greater the mechanical inspiratory flow rate, the more PIP measured at the "Y" piece overestimates pressure at proximate the distal end of the endotracheal tube. This becomes especially critical when dealing with intubated pediatric patients.

The conventional pressure measuring sites also compromise the responsiveness of the conventional respiratory systems to patient inspiratory efforts. This produces delays in triggering the supply of inspiratory assist "on" and cycling "off," predisposing the patient to patient-respiratory system dysynchrony, and can dramatically increase the effort or work to inhale. Significantly less imposed work results from pressure triggering and controlling the respiratory system "on" at the distal end of the endotracheal tube compared with the conventional method of pressure triggering and controlling or by using Flow-By™. Flow-By™ is a method introduced by the Mallingckrodt Nellcor Puritan-Bennett Company that uses flow sensitivity to trigger the ventilator "on" instead of pressure sensitivity. Whether pressure triggering from inside the ventilator or using Flow-By™, an initial pressure drop across the endotracheal tube must be generated by the patient to initiate flow. This effort results in significant increases in imposed resistive work of breathing. Conventional respiratory systems introduce other more complex factors contributing to $WOB_i$: the work to trigger the ventilator "on" (i.e., to initiate flow), the relative flow or pressure target used during the post trigger phase, and breath termination or cycling "off" criteria.

Thus, the design of conventional respiratory systems results in respiratory support systems that are predisposed to increase $WOB_i$ or have limited ability to decrease the $WOB_i$. The conventional designs also fail to provide any reliable degree of automatic responsiveness. To compensate, modern conventional respiratory systems contain complicated control algorithms so that the ventilators can "approximate" what is actually occurring within the patient's lungs on a breath-by-breath basis. In effect, the computer controlled prior art respiratory systems are limited to the precise, and unyielding, nature of the mathematical algorithms which attempted to mimic cause and effect in the ventilator support provided to the patient. Ventilatory support should be tailored to each patient's existing pathophysiology and should both provide automatic and variable levels of pressure assist in response to patient inspiratory demand and should minimize $WOB_i$. Such a respiratory system is unavailable in current ventilators.

SUMMARY

In accordance with the purposes of this invention, as embodied and broadly described herein, this invention, in one aspect, relates to a respiratory system that supplies a pressurized breathing gas from a pressurized gas source to a patient via a breathing circuit in fluid communication with the lungs of a patient. The breathing circuit includes an endotracheal tube, an inhalation conduit in fluid communication with the proximal end of the endotracheal tube, and an exhalation conduit in fluid communication with the proximal end of the endotracheal tube. The respiratory system includes a demand valve in selective fluid communication with the pressurized gas source and the inhalation conduit and a tracheal pressure conduit in fluid communication with the distal end of the endotracheal tube and a reference camber.

The demand valve is movable between a first position, in which the demand valve is opened so that the inhalation conduit is placed in fluid communication with the pressurized gas source, and a second position, in which the demand valve is closed so that the inhalation conduit is not in fluid communication with the pressurized gas source. The respiratory system further includes a means for proportionally opening the demand valve in response to pressure changes within the reference chamber so that $WOB_i$ is automatically nullified by providing levels of inspiratory pressure assist that are automatic and proportional on demand of the patient.

DETAILED DESCRIPTION OF THE FIGURES OF THE DRAWINGS

The accompanying drawings, which are incorporated in and constitute a part of this specification, illustrate several embodiments of the invention and together with the description, serve to explain the principals of the invention.

DETAILED DESCRIPTION OF THE INVENTION

The present invention is more particularly described in the following examples that are intended to be illustrative only since numerous modifications and variations therein will be apparent to those skilled in the art. As used in the specification and in the claims, the singular form "a," "an" and "the" include plural referents unless the context clearly dictates otherwise.

Figure 1:
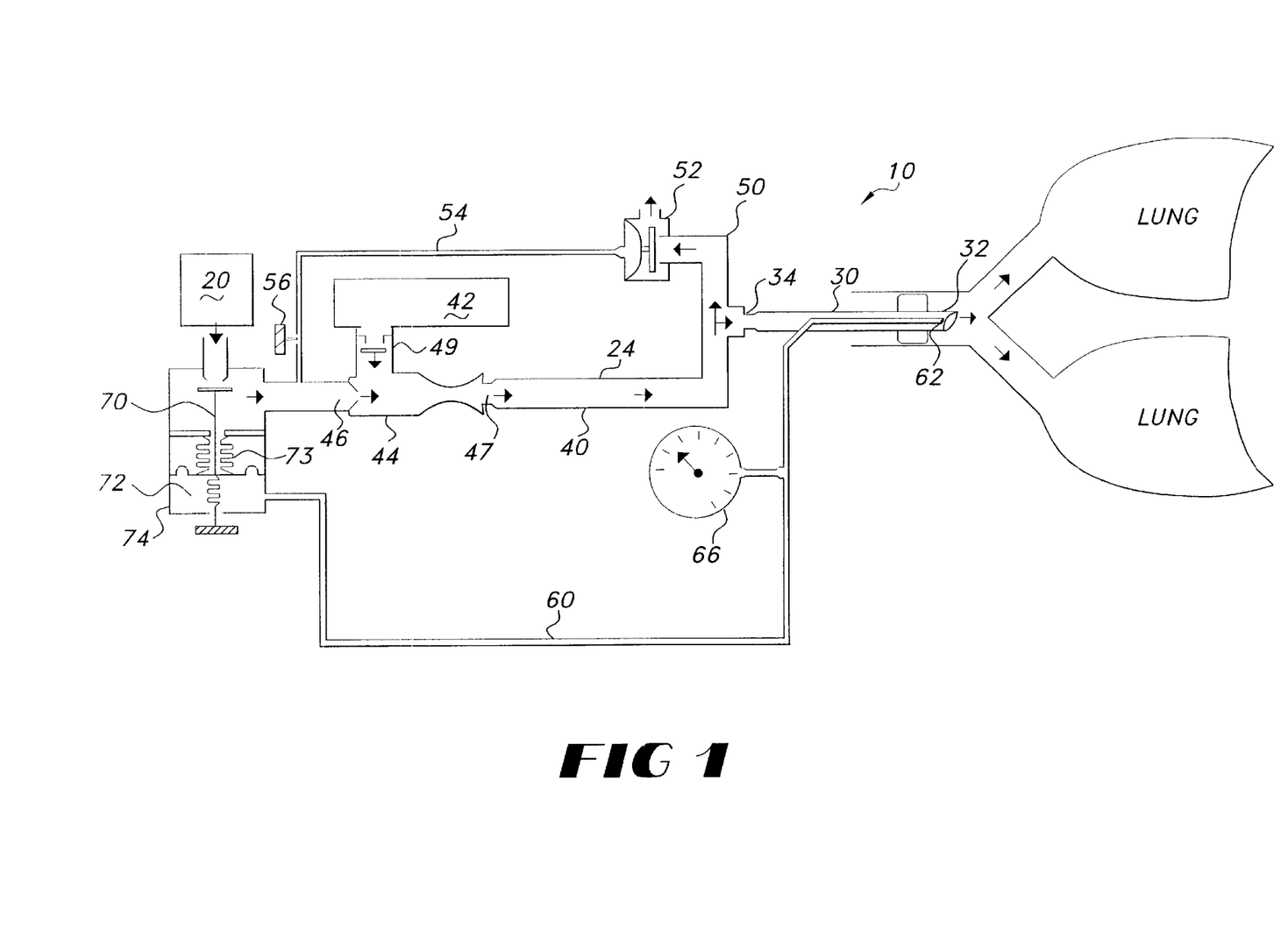
FIG. 1 is a schematic diagram of an exemplified structure of the present invention.

As depicted in FIG. 1, the respiratory system 10 of the present invention preferably comprises a pressurized gas source 20, a breathing circuit 24, a tracheal pressure conduit 60, and a demand valve 70. The breathing circuit 24 includes an endotracheal tube 30, an inhalation conduit 40, and an exhalation conduit 50. The endotracheal tube 30 has a distal end 32 and a proximal end 34. In use, the distal end 32 is placed within the trachea of the patient to be in fluid communication with the patient's lungs. The inhalation conduit 40 is in fluid communication with the proximal end 34 of the endotracheal tube 30. In like fashion, the exhalation conduit 50 is in fluid communication with the proximal end 34 of the endotracheal tube 30. The exhalation conduit 50 includes an exhalation valve 52 that is in selective fluid communication with the atmosphere. To connect the respective inhalation and exhalation conduits 40, 50 to the proximal end 34 of the endotracheal tube 30, a "Y"-piece, for example, may be used. The tracheal pressure conduit 60 is in fluid communication with the distal end 32 of the endotracheal tube 30 and a reference chamber 72.

The demand valve 70 is in selective fluid communication with the pressurized gas source 20 and the inhalation conduit 40. The demand valve 70 is proportionally movable between a first position during inhalation, in which the demand valve 70 is opened so that the inhalation conduit 40 is placed in fluid communication with the pressurized gas source 20, and a second position during exhalation, in which the demand valve is closed so that the inhalation conduit 40 is not in fluid communication with the pressurized gas source 20. The respiratory system 10 further includes a means for proportionally opening the demand valve 70 in response to pressure changes within the reference chamber 72.

The opening means opens and closes the demand valve 70 in proportion to a preselected baseline pressure. Thus, during inhalation, a drop in fluid pressure proximate the distal end 32 of the endotracheal tube 30 is communicated to the reference chamber 72 via the tracheal pressure conduit 60 so that the demand valve 70 opens proportionally upon a pressure drop in the reference chamber 72 relative to the baseline pressure. During exhalation, a rise in fluid pressure proximate the distal end 32 of the endotracheal tube 30 is similarly communicated to the reference chamber 72 via the tracheal pressure conduit 60 so that the demand valve 70 closes when pressure within the reference chamber 72 is equal to or greater than the baseline pressure.

Such an opening means, demand valve 70, and reference chamber 72 may comprise portions of a pressure regulator 74 whose control system detects a drop/rise in pressure with respect to the baseline pressure. Such pressure regulators 74 are known to one skilled in the art and is of a type that is exemplified by a Bird #4715 Baseline Compensator Pressure Regulator. The demand valve 70 of the pressure regulator 74 may be adjustable so that the setting of the baseline pressure is operator-selectable. This allows the operator of the respiratory system to manually select the desired level of CPAP (as the baseline pressure) supplied by the respiratory system 10. The pressure regulator 74 may also include a spring 73 operatively connected to the demand valve 70 for assisting the opening of the demand valve 70.

The inhalation conduit 40 of the respiratory system 10 may also comprise a gas reservoir 42 and a venturi tube 44. The venturi tube 44 has an inlet 46, and outlet 47, and an augmentation valve 49. Such a venturi tube 44 is known to one skilled in the art and is of a type that is exemplified by Bird 6549, 2027, 2029 Venturi with One-Way Valves. The inlet 46 of the venturi tube 44 is in fluid communication with the demand valve 70 and the outlet 47 of the venturi tube 44 is in fluid communication with the proximal end 34 of the endotracheal tube 30. The augmentation valve 49 is in fluid communication with the gas reservoir 42. The gas reservoir 42 has the same relative percentage mixture of gases as the pressurized gas source 20. The augmentation valve 49 is movable between a closed position during exhalation, in which the venturi tube 44 is not in fluid communication with the gas reservoir 42, and an opened position during inhalation, in which the venturi tube 44 is placed in fluid communication with the gas reservoir 42. In use, when gas from the pressurized gas source 20 enters the inlet 46 of the venturi tube 44 when the demand valve 70 is opened, i.e., during inhalation, the augmentation valve 49 allows gas of the same relative composition to be drawn from the gas reservoir 42 to augment the flow of gas that, in turn, exits the outlet 47 of the venturi tube 44. Thus, the venturi tube 44 acts as a flow amplifier to increase the flow of gas supplied via the inhalation conduit 40 to the proximal end 34 of the endotracheal tube 30.

The exhalation valve 52 of the exhalation conduit 50 may also have an exhalation valve control conduit 54 that is in fluid communication with the inhalation conduit 40 intermediate the inlet 46 of the venturi tube 44 and the demand valve 70. Such an exhalation valve 52 having a port for communication to an exhalation valve control conduit 54 is known in the art and is of a type that is exemplified by a Bird #2757 Exhalation Valve. During exhalation, the pressure within the inhalation 40 conduit drops because the demand valve 70 is closed, which therefore causes the pressure in the exhalation valve control conduit 54 to drop. The exhalation valve 52 is responsive to pressure in the exhalation valve control conduit 54 so that, during exhalation, the exhalation valve 52 opens in proportion to the pressure drop in the exhalation valve control conduit 54 relative to the pressure of gas within the exhalation conduit 50. When opened, the exhalation valve 52 allows fluid within the exhalation conduit 50 to vent to the atmosphere. Conversely, during inhalation, the pressure within the inhalation conduit 40, and thus the pressure within the exhalation valve control conduit 54, increases, which closes the exhalation valve 52 when pressure in the exhalation valve control conduit 54 is equal to or greater than pressure in the exhalation conduit 50.

To provide a means for controlling the resistance of the exhalation valve 52 to opening, the exhalation valve control conduit 54 may have a selectable restrictor valve 56 which controls the resistance of the exhalation valve 52 to proportionally open. The restrictor valve 56 is moveable from an open position, in which fluid flow into the exhalation valve control conduit 54 is unrestricted, towards a closed position, in which the exhalation valve control conduit 54 is obstructed so that fluid flow into the exhalation valve control conduit 54 is restricted. As one skilled in the art will appreciate, if the exhalation valve control conduit 54 is unrestricted, the exhalation valve 52 must overcome the resistance of the pressure within the exhalation valve control conduit 52 in order to proportionally open into fluid communication with the atmosphere. As the exhalation valve control conduit 54 is restricted by actuating the restrictor valve 56, the flow of gas into the exhalation valve control conduit 54 decreases, which decreases the resistance of the exhalation valve 52 to opening. Thereby, as one skilled in the art will appreciate, when the resistance of the exhalation valve 52 decreases, the exhalation valve 56 may proportionally open at a lower pressure within the exhalation conduit 50 relative to the pressure required within the exhalation conduit 50 to open the exhalation valve 52 if the exhalation valve control conduit 54 is unrestricted.

The respiratory system 10 may also comprise a pressure sensor 66 having an indicator to display pressure. The pressure sensor 66 is in fluid communication with the tracheal pressure conduit 60 so that pressure within the tracheal pressure conduit 60 and the reference chamber 72 may be displayed. The displayed pressure allows the operator to determine if the respiratory system 10 is maintaining pressure at the distal end 32 of the endotracheal tube 30 as the proximate level of the baseline pressure (i.e., the desired level of CPAP) set in the selectable demand valve 70.

In operation, the respiratory system 10 preferably operates on the basis of closed-loop feedback control. Pressurized gas flow on spontaneous inspiratory demand of the patient is directed from the pressurized gas source 20 via the demand valve 70 through the inhalation conduit 40 and endotracheal tube 30 to the lungs of the patient. The exhalation valve 52 is pressurized closed during inhalation and functions as a threshold resistor for maintaining CPAP during exhalation. Tracheal pressure at the distal end 32 off the endotracheal tube 30 is communicated back to the reference chamber 72 via the tracheal pressure conduit 60 and is used for triggering the respiratory system 10 "ON" by opening the demand valve 70, controlling the inspiratory assist pressure by proportionally controlling the demand valve 70, and cycling "OFF" the respiratory system 10 by closing the demand valve 70.

Figure 2:
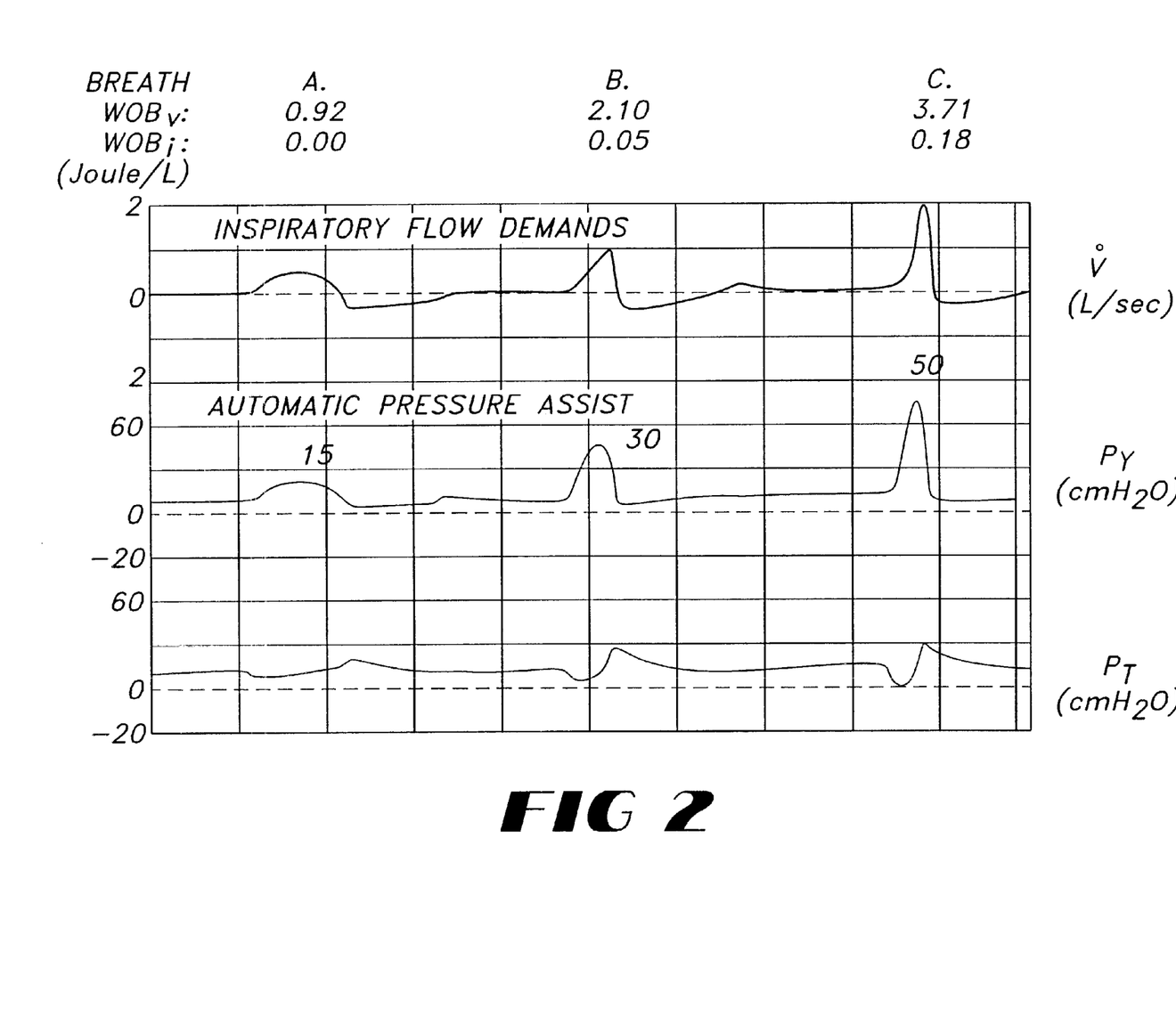
FIG. 2 shows the relationship between the patient inspiratory flow demands, the automatic and variable levels of inspiratory pressure assist applied by the respiratory system of the present invention to minimize inspiratory imposed resistive work of breathing ($WOB_i$), and the pressure proximate the distal end of an endotracheal tube in communication with the lungs of the patient.

As shown in FIG. 2, the inspiratory assist pressure is automatic and variable on demand, i.e., the greater the demand-flow, the greater the inspiratory assist pressure and the ventilator work of breathing ($WOB_V$) to minimize the inspiratory imposed resistive work of breathing ($WOB_i$). In the illustrated examples "A," "B," and "C," peak inspiratory flow rate demands (V) increase from example "A" to example "C." The respiratory system 10 responds by automatically providing increasing inspiratory assist pressures to match the increasing peak inspiratory flow rate demands. Breathing circuit pressure measured at the "Y" piece ($P_Y$), adjacent the proximal end 34 of the endotracheal tube 30 is increased in response to the increased inspiratory flow rate demands. The pulmonary airway pressure, which is reflected by the tracheal pressure ($P_T$) measured at the distal end 32 of the endotracheal tube 30, is not increased. Thus, in operation, the greater the inspiratory flow rate demand, the greater the inspiratory assist pressure supplied by the respiratory system 10 to minimize the inspiratory imposed resistive work of breathing ($WOB_i$), and vice versa.

Figure 3:
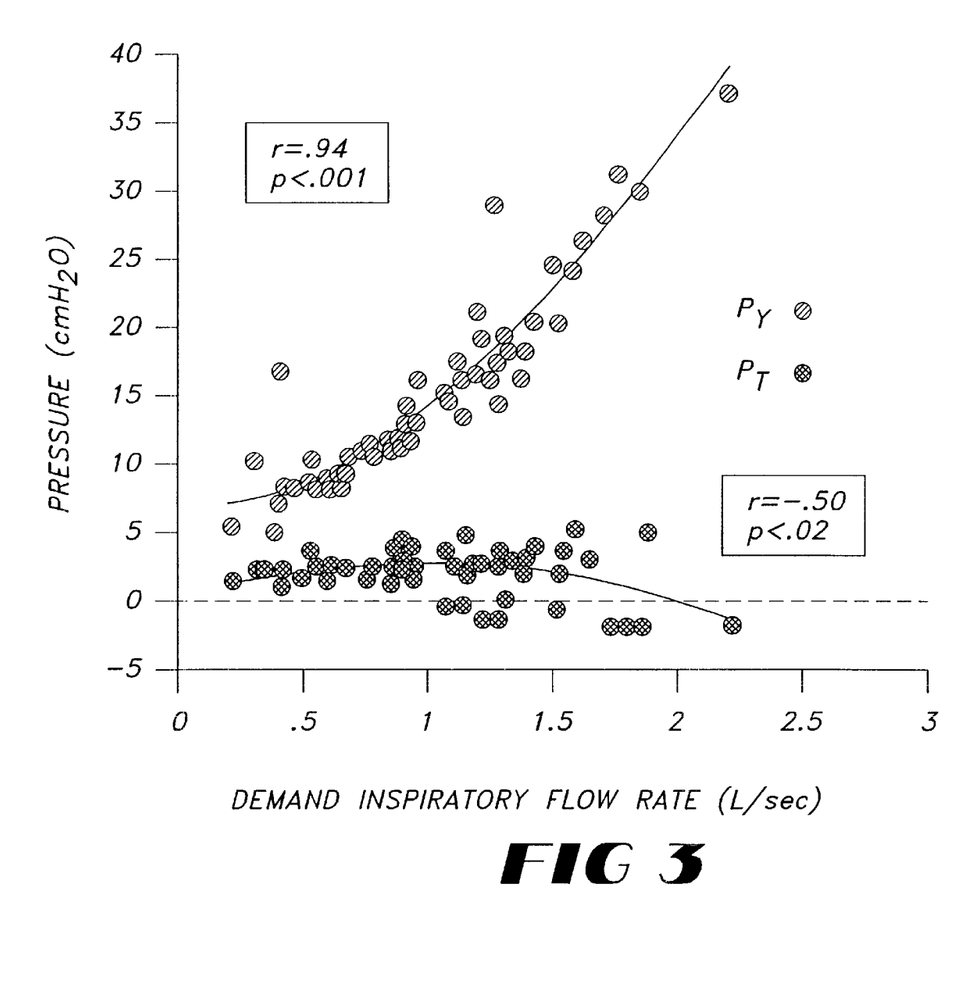
FIG. 3 shows the relationship between inspiratory assist pressures measured at the "Y" piece ($P_Y$) of the breathing circuit proximate the proximal end of the endotracheal tube and proximate the distal end of the endotracheal tube ($P_T$) and peak spontaneous inspiratory flow rate demands.

The relationship between inspiratory assist pressures measured at the "Y" piece ($P_Y$) and at the distal end 32 of the endotracheal tube 30 ($P_T$) and peak spontaneous inspiratory flow rate demands is illustrated in FIG. 3. The respiratory system 10 automatically and directly varies inspiratory assist pressure levels in response to flow rate demands. Pulmonary airway pressure, as reflected by $P_T$, varies inversely with flow rate demands and are maintained a fairly constant levels at low to moderate flow rate demands and demonstrate a slight decreasing trend at higher flow rate demands. As noted previously, breathing circuit pressures, as reflected by $P_Y$, are substantially greater than $P_T$ especially under high flow rate demands.

Figure 4:
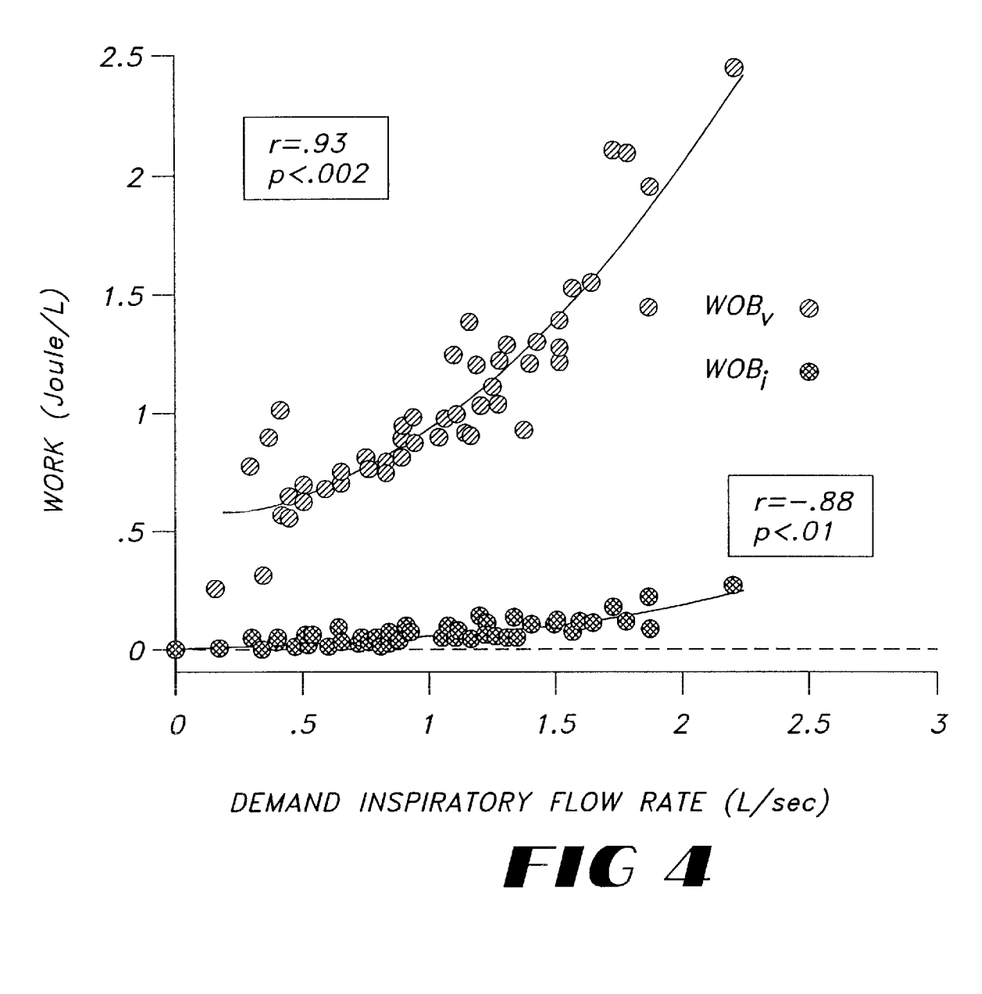
FIG. 4 shows the relationship between work of breathing provided by the respiratory system to assist inhalation ($WOB_v$), inspiratory imposed resistive work of breathing ($WOB_i$), and peak spontaneous inspiratory flow rate demands.

Referring now to FIG. 4, the relationships between work of breathing provided by the respiratory system 10 to assist inhalation ($WOB_V$), inspiratory imposed resistive work of breathing ($WOB_i$), and peak spontaneous inspiratory flow rate demands are shown. $WOB_V$ varies automatically and directly with flow rate demands. Breathing apparatus imposed resistive workloads, as reflected by $WOB_i$, are nullified at low and moderate flow rate demands and demonstrate a slight increasing trend at higher flow rate demands.

Figure 5A:
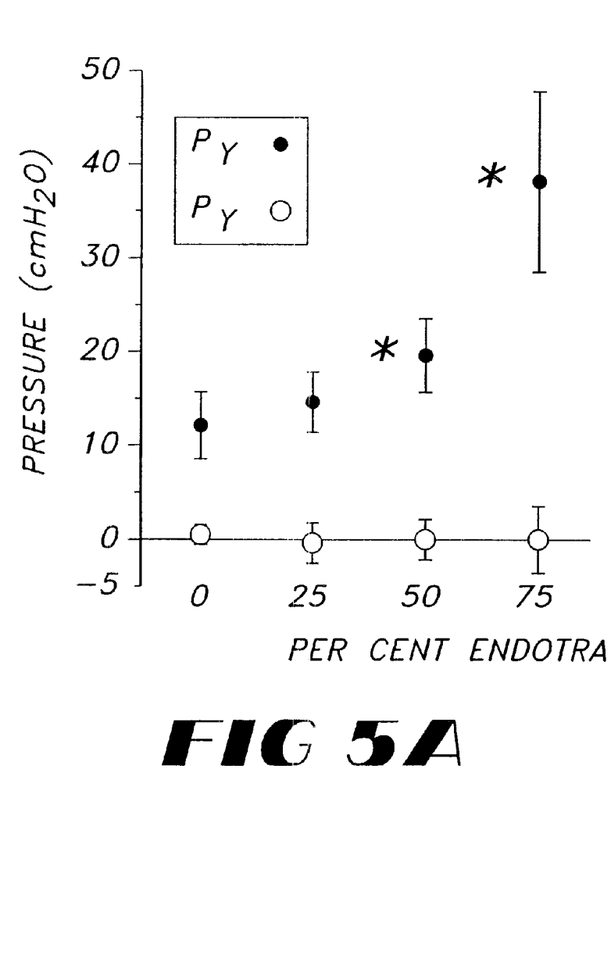
FIG. 5A shows the relationship between $P_Y$, $P_T$, and percent occlusion of the endotracheal tube.
Figure 5B:
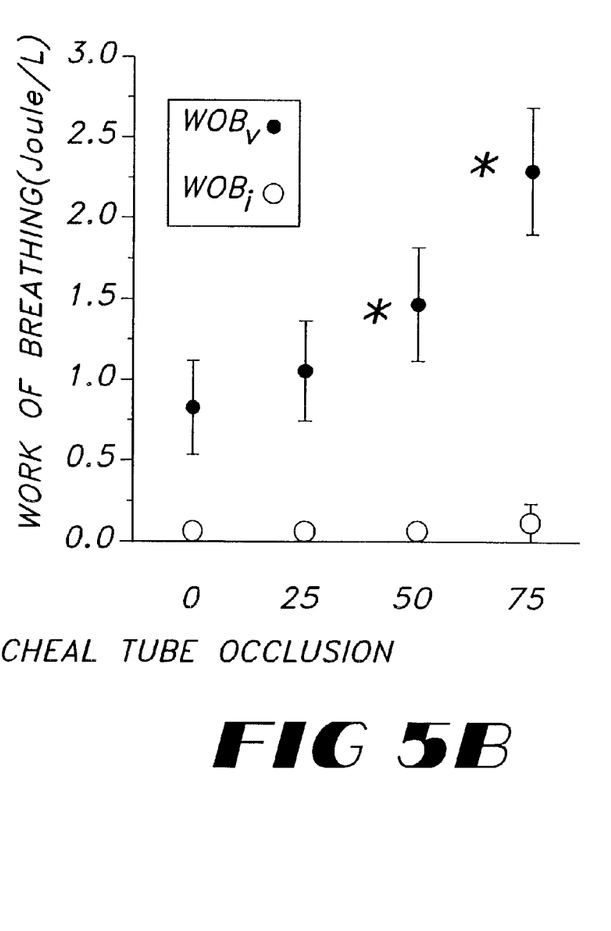
FIG. 5B shows the relationship between $WOB_v$, $WOB_i$, and percent occlusion of the endotracheal tube.

The respiratory system 10 also automatically and variably adjusts for partial endotracheal tube occlusion. Partial endotracheal tube occlusion by secretions significantly increases imposed resistive work across the endotracheal tube 30 and poses a significant threat to intubated patients, especially patients presenting with copious amount of secretions. Substantial deposits of secretions narrow the internal diameter of the endotracheal tube which results in significant increases in resistance and work. In conventional respiratory systems, this results in inappropriately low levels of pressure assist being provided which elevates the imposed work of breathing and predisposes the patient to respiratory muscle fatigue. Referring to FIGS. 5A and 5B, because $P_T$ is measured directly and the triggering site of the respiratory system 10 is at the distal end 32 of the endotracheal tube 30 which is disposed within the patient's trachea, the respiratory system 10 provides automatic and variable levels of pressure assist to overcome the breathing apparatus impedance, including the increased impedance of the partially occluded endotracheal tube, and to satisfy inspiratory flow rate demands of the patient. With partial endotracheal tube occlusion, the level of pressure assist increases proportionally, nullifying the increased imposed resistive work of breathing ($WOB_i$). The greater the impedance and flow rate demand to inhale, the greater the pressure assist and ventilator work of breathing ($WOB_V$) to minimize the imposed work of breathing ($WOB_i$), and vice versa.

Figure 6:
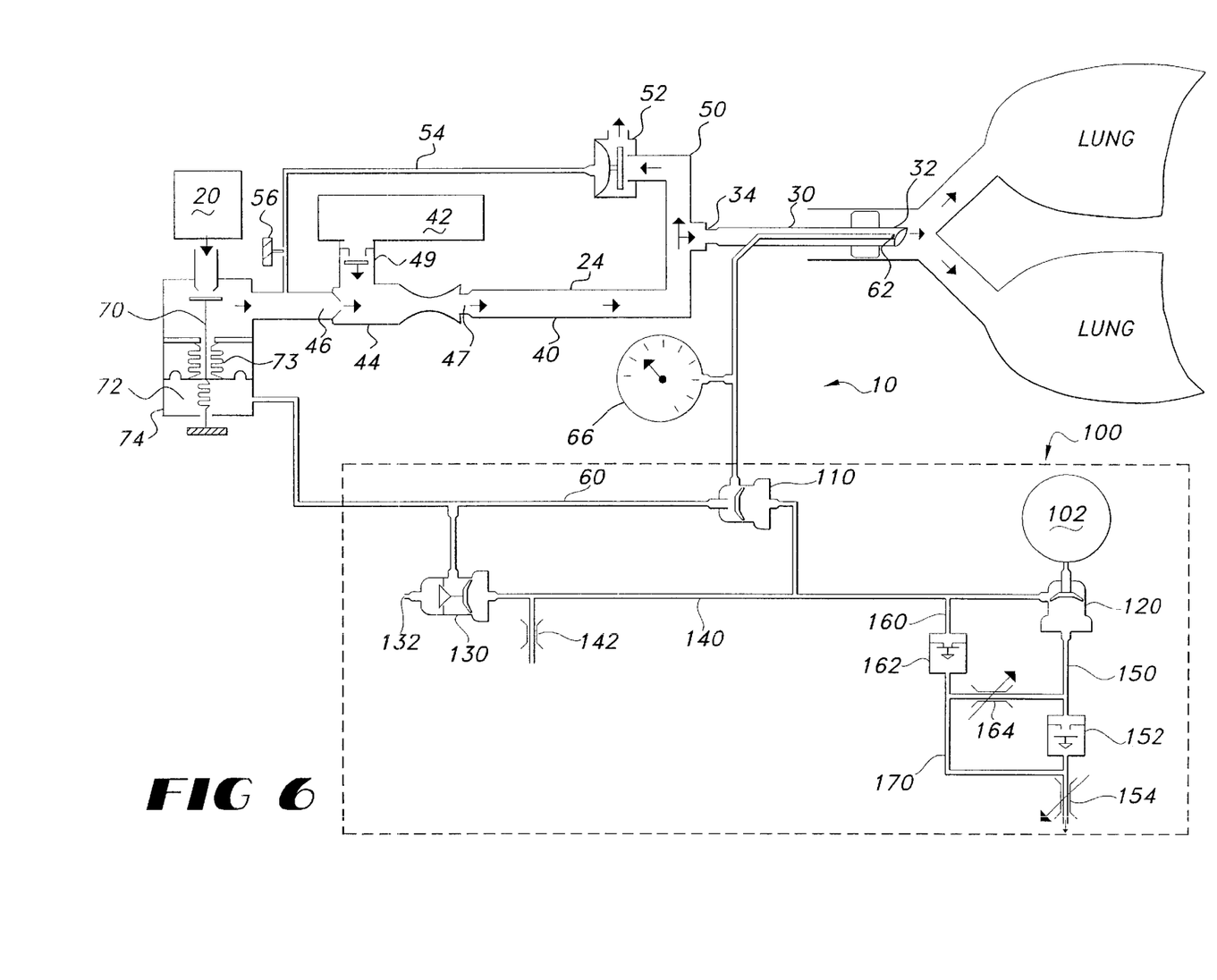
FIG. 6 is a schematic diagram of an exemplified structure of the present invention including a mandatory breath support ventilation subsystem, the mandatory breath support ventilation subsystem shown in a first position, in which gas from a pressurized gas source in supplied to an inhalation conduit upon patient demand for a predetermined expiratory time interval.
Figure 7:
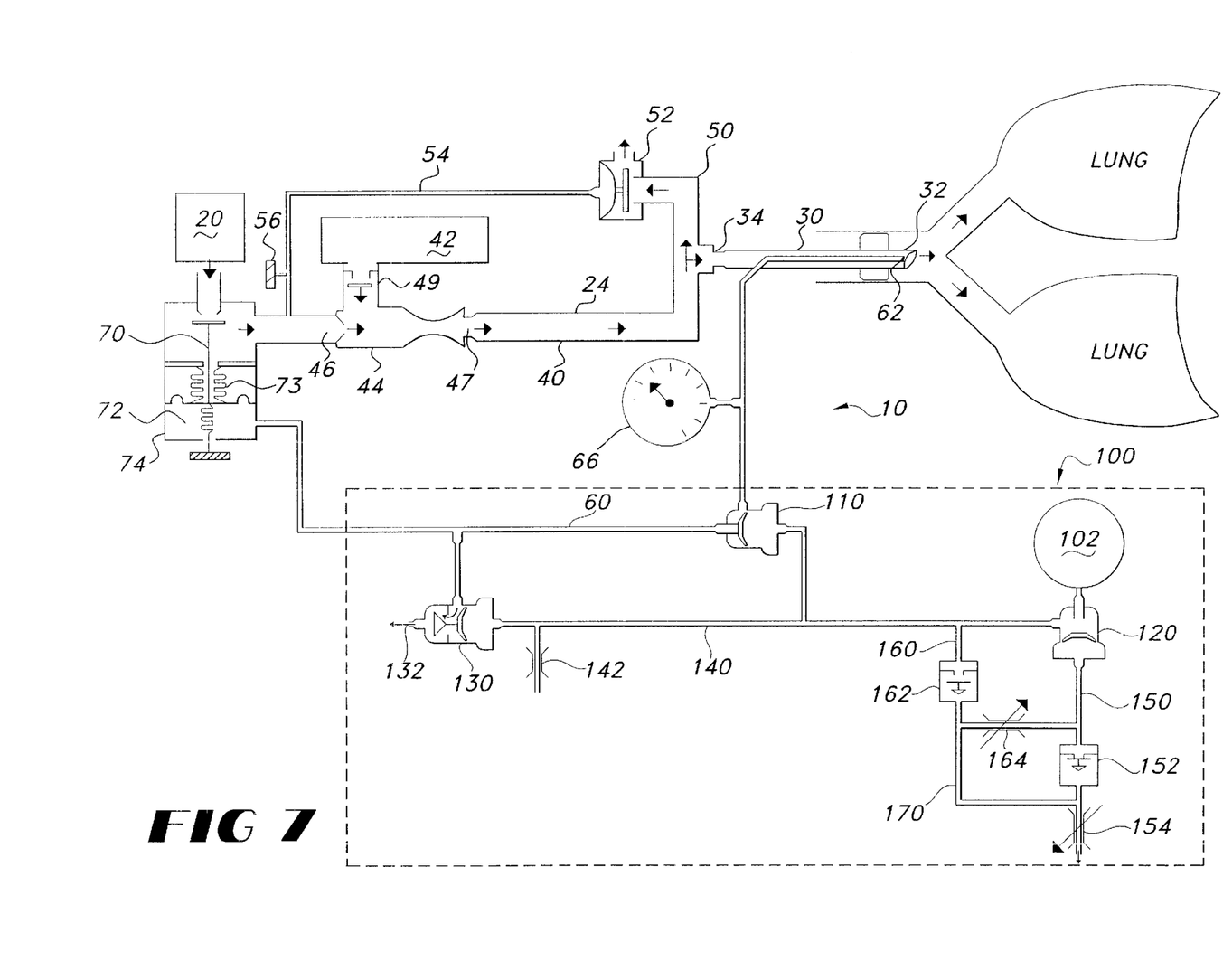
FIG. 7 is a schematic diagram of an exemplified structure of the present invention including a mandatory breath support ventilation subsystem, the mandatory breath support ventilation subsystem shown in a second position, in which gas within a reference chamber is vented to atmosphere and gas from the pressurized gas source is supplied to an inhalation conduit for a predetermined inspiratory time interval.

Referring to FIGS. 6 and 7, the respiratory system may include a mandatory breath support ventilation subsystem 100 for providing mechanical ventilatory support to apneic subjects or those requiring periodic breaths to augment spontaneous breathing. The respiratory system 10, via the mandatory breath support ventilation subsystem 100, may provide conventional mechanical ventilation (CMV) and intermittent mandatory ventilation (IMV).

The mandatory breath support ventilation subsystem 100 permits the respiratory system to function as a time cycled mechanical ventilator. With this type of ventilator, tidal volume is the product of inspiratory flow rate and inspiratory time, i.e., Tidal Volume (ml)=Inspiratory Flow Rate (ml/sec)×Inspiratory Time (sec).

During mechanical inhalation with the respiratory system 10 of the present invention, gas flow rate is substantially constant while inspiratory time is variable. Thus, by regulating inspiratory time, tidal volume may be regulated. Following mechanical inhalation, the respiratory system 10 provides ventilator support in the manner described previously, automatically and variably supplying levels of inspiratory assist pressure to minimize $WOB_i$. "The mandatory breath support ventilation subsystem 100 allows gas from the pressurized gas source 20 to pass into the inhalation conduit 40 to the patient for a predetermined inspiratory time interval. The mandatory breath ventilation subsystem 100 comprises a mandatory breath ventilation subsystem source of pressurized gas 102, a first normally-open cartridge valve 110, a second normally-open cartridge valve 120, a normally-closed cartridge valve 130, a fluid conduit 140, an exhalation fluid line 150, an inhalation fluid line 160, and a back-pressure conduit 170."

The first normally-open cartridge valve 110 is connected to the tracheal pressure conduit 60 and in its normally open position allows fluid to be communicated from the distal end 32 of the endotracheal tube 30 to the reference chamber 72. When pressurized closed, the first normally-open cartridge valve 110 closes the tracheal pressure conduit 60 to prevent communication of fluid from the distal end 32 of the endotracheal tube 30 to the reference chamber 72. The second normally-open cartridge valve 120 is connected to the source of pressurized gas 102. As one skilled in art will appreciate, the source of pressurized gas 102 may be a separate pressurized gas source or it may be the same pressurized gas source 20 that is in communication with the demand valve.

The normally-closed cartridge valve 130 is connected to the tracheal pressure conduit 60 between the first normally-open cartridge valve 110 and the reference chamber 72. The normally-closed cartridge valve 130 has an outlet port 132 in selective fluid communication with the atmosphere. When pressurized open, the normally-closed cartridge valve 130 allows the reference chamber 72 to be in fluid communication with the atmosphere through the outlet port 132. The first and second normally-open cartridge valves 110, 120 and the normally-closed cartridge valve 130 are pressure actuated valves that are well known in the art and are exemplified by Bird #6830 and #6668 normally-open and normally-closed cartridge valves.

The fluid conduit 140 is connected to the first normally-open cartridge valve 110, the second normally-open cartridge valve 120, and the normally-closed cartridge valve 130. The fluid conduit 140 acts as a central line to conduit fluid from the source of pressurized gas 102 to various components of the mandatory breath ventilation subsystem 100. The fluid conduit 140 also has a fluid conduit line resistor 142 in selective fluid communication with the atmosphere. The fluid conduit line resistor 142 allows fluid in the fluid conduit 140 to be selectively vented to the atmosphere.

The exhalation fluid line 150 is connected to the second normally-open cartridge valve 120. The exhalation fluid line 150 has a first one-way valve 152 and an expiratory resistor 154. The first one-way valve 152 is positioned intermediate the second normally-open cartridge 120 and the expiratory resistor 154, i.e., upstream of the expiratory resistor 154, and is oriented to allow fluid flow within the exhalation fluid line 150 downstream toward the expiratory resistor 154. The expiratory resistor 154 is in selective fluid communication with the atmosphere.

The inhalation fluid line 160 is connected to the fluid conduit 140 and to the exhalation fluid line 150 intermediate the second normally-open cartridge valve 120 and the first one-way valve 152. The inhalation fluid line 160 has a second one-way valve 162 and an inhalation resistor 164. The second one-way valve 162 is positioned intermediate the fluid conduit 140 and the inhalation resistor 164, i.e., upstream of the inhalation resistor 164, and is oriented to allow fluid flow within the inhalation fluid line 160 downstream toward the inhalation resistor 164. The inhalation resistor 164 is in selective fluid communication with the exhalation fluid line 150.

The inhalation fluid line 160 and the exhalation fluid line 150 are interconnected by the back-pressure conduit 170. The back-pressure conduit 170 is connected to the exhalation fluid line 150 intermediate the first one-way valve 152 and the exhalation resistor 154 and is connected to the inhalation fluid line 160 intermediate the second one-way valve 162 and the inhalation resistor 164.

The mandatory breath support ventilation subsystem 100 is switchable from a first position, as shown in FIG. 6, in which gas from the pressurized gas source 20 is supplied to the inhalation conduit 40 upon demand of the patient for a predetermined expiratory time interval, to a second position, as shown in FIG. 7, in which the reference chamber 72 of the pressure regulator 74 is vented to the atmosphere through the outlet port 132 of the normally-closed cartridge valve 130. In the second position, because the pressure of gas within the vented reference chamber 72 is less than the baseline pressure, gas from the pressurized gas source 20 is supplied to the inhalation conduit 40 for the predetermined inspiratory time interval.

Referring to FIG. 6, in the first position, the first normally-open cartridge valve 110 is open so that the distal end 62 of the tracheal pressure conduit 60 is in fluid communication with the reference chamber 72 of the pressure regulator 74, the second normally-open cartridge valve 120 is closed so that the source of pressurized gas 102 is not in fluid communication with the fluid conduit 140, and the normally-closed cartridge valve 130 is closed so that the reference chamber 72 of the pressure regulator 74 is not in fluid communication with the atmosphere. In operation, during spontaneous inhalation by the patient, tracheal pressure is directed back through the first normally-open cartridge valve 110 via the tracheal pressure conduit 60 to the reference chamber 72. The respiratory system 10 responds to changes in the pressure within the reference chamber 72 relative to the baseline pressure as described previously. The second normally-open cartridge valve 120 blocks off pressurized gas 102 from the source of pressurized gas and is allowed to gradually depressurize via fluid being vented from the exhalation fluid line 150 through the exhalation resistor 154 to the atmosphere over the predetermined expiratory time interval ($T_E$). The exhalation resister 154 governs the rate of depressurization of the second normally-open cartridge 120 and depressurizes the second normally-open cartridge 120 over the predetermined expiratory time interval ($T_E$).

Referring now to FIG. 7, in the second position, the first normally-open cartridge valve 110 is closed so that the distal end 62 of the tracheal pressure conduit 60 is not in fluid communication with the reference chamber 72 of the pressure regulator 74, the second normally-open cartridge valve 120 is opened so that the source of pressurized gas 102 is in fluid communication with the fluid conduit 140, and the normally-closed cartridge valve 130 is opened so that the reference chamber 72 of the pressure regulator 74 is in fluid communication with the atmosphere. In operation, when the exhalation fluid line 150 is depressurized at the end of the expiratory time interval $T_E$, the second normally-open cartridge valve 120 is depressurized and is opened by the source of pressurized gas 102 which, via the fluid conduit 140, simultaneously pressurizes closed the first normally-open cartridge valve 110 and opens the normally-closed cartridge valve 130. Opening the normally-closed cartridge valve 130 permits the reference chamber 72 to depressurize as it vents to the atmosphere. Because the pressure of gas within the vented reference chamber 72 is less than the baseline pressure, gas from the pressurized gas source 20 is supplied to the inhalation conduit 40 and to the exhalation valve 52 via the exhalation valve control conduit 54 to pressurize the exhalation valve 52 closed. This results in the lungs of the patient being actively inflated (i.e., mechanical inhalation). While the lungs of the patient are being actively inflated, pressurized gas from the source of pressurized gas 102 is flowing through the inhalation fluid line 160 and the back-pressure conduit 170. The gas flowing through the inhalation fluid line 160 flows through the first second-way valve 162 and the downstream inhalation resistor 164 that regulates the predetermined inspiratory time interval ($T_I$). The inhalation resister 164 governs the rate of repressurization of the second normally-open cartridge 120 and repressurizes the second normally-open cartridge 120 over the predetermined inspiratory time interval ($T_I$). When the second normally-open cartridge 120 is repressurized at the end of the inspiratory time interval ($T_I$), the mandatory breath ventilation subsystem 100 is placed back at the first position, as shown in FIG. 6, so that spontaneous breathing by the patient is once again permitted.

The inhalation and exhalation resistors 164, 154 of the mandatory breath support ventilation subsystem 100 may be adjustable so that the predetermined inspiratory time interval and the predetermined expiratory time interval are selectable by the operator. The resistors are well known in the art and are exemplified by Industrial Specialties #RR-16-025 and #RR-16-012 resistors.

The invention has been described herein in considerable detail, in order to comply with the Patent Statutes and to provide those skilled in the art with information needed to apply the novel principles, and to construct and use such specialized components as are required. However, it is to be understood that the invention can be carried out by specifically different equipment and devices, and that various modification, both as to equipment details and operating procedures can be affected without departing from the scope of the invention itself. Further, it should be understood that, although the present invention has been described with reference to specific details of certain embodiments thereof, it is not intended that such details should be regarded as limitations upon the scope of the invention except as and to the extent that they are included in the accompanying claims.

What is claimed is:

1. A respiratory system comprising:
   a. an endotracheal tube having a proximal end and a distal end;
   b. a tracheal pressure conduit in fluid communication with the distal end of the endotracheal tube;
   c. an inhalation conduit in fluid communication with the proximal end of the endotracheal tube;
   d. an exhalation conduit having an exhalation valve, the exhalation conduit in fluid communication with the proximal end of the endotracheal tube;
   e. a pressurized gas source; and
   f. a pressure regulator having a reference chamber and a demand valve in selective fluid communication with the pressurized gas source and the inhalation conduit, wherein the reference chamber is in fluid communication with the tracheal pressure conduit, wherein the demand valve is responsive to pressure within the reference chamber to open and close in proportion to a baseline pressure, wherein the demand valve is proportionally moveable between a first position during inhalation, in which the demand valve is opened so that the inhalation conduit is in fluid communication with the pressurized gas source, and a second position during exhalation, in which the demand valve is closed so that the inhalation conduit is not in fluid communication with the pressurized gas source, and wherein the demand valve opens proportionally upon a pressure drop in the reference chamber relative to the baseline pressure and is closed when pressure in the reference chamber is equal to or greater than the baseline pressure.

2. The respiratory system of claim 1, wherein the inhalation conduit further comprises a gas reservoir and a venturi tube having an inlet, an outlet, and an augmentation valve, the inlet of the venturi tube in fluid communication with the demand valve and the outlet of the venturi tube in fluid communication with the proximal end of the endotracheal tube, wherein the augmentation valve is in fluid communication with the gas reservoir.

3. The respiratory system of claim 2, wherein the augmentation valve is movable between a closed position during exhalation, in which the venturi tube is not in fluid communication with the gas reservoir, and an opened position during inhalation, in which the venturi tube is in fluid communication with the gas reservoir.

4. The respiratory system of claim 2, wherein the exhalation valve of the exhalation conduit has an exhalation valve control conduit in fluid communication with the inhalation conduit intermediate the inlet of the venturi tube and the demand valve of the pressure regulator, the exhalation valve responsive to pressure in the exhalation valve control conduit so that the exhalation valve opens in proportion to a pressure drop in the exhalation valve control conduit relative to pressure in the exhalation conduit and is closed when pressure in the exhalation valve control conduit is equal to or greater than pressure in the exhalation conduit.

5. The respiratory system of claim 4, wherein the exhalation valve control conduit has a selectable restrictor valve movable from an open position, in which fluid flow through the exhalation valve control conduit is unrestricted, towards a closed position, in which fluid flow through the exhalation valve control conduit is restricted so that, when the exhalation valve control conduit is restricted, resistance of the exhalation valve to open is lowered.

6. The respiratory system of claim 1, wherein the demand valve of the pressure regulator is adjustable so that the baseline pressure is selectable.

7. The respiratory system of claim 1, further comprising a pressure sensor having an indicator to display pressure, the pressure sensor in fluid communication with the tracheal pressure conduit so that pressure within the tracheal pressure conduit may be displayed.

8. The respiratory system of claim 1, further comprising a mandatory breath support ventilation subsystem to supply gas from the pressurized gas source to the inhalation conduit at a predetermined inspiratory time interval and a predetermined expiratory time interval.

9. The respiratory system of claim 8, wherein the mandatory breath ventilation subsystem comprises:
   a. a mandatory breath ventilation subsystem source of pressurized gas;
   b. a first normally-open cartridge valve connected to the tracheal pressure conduit;
   c. a second normally-open cartridge valve connected to the mandatory breath ventilation subsystem source of pressurized gas;
   d. a normally-closed cartridge valve connected to the tracheal pressure conduit intermediate the first normally-open cartridge valve and the reference chamber of the pressure regulator, the normally-closed cartridge valve having an outlet port in selective fluid communication with atmosphere;
   e. a fluid conduit connected to the first normally-open cartridge valve, the second normally-open cartridge valve, and the normally-closed cartridge valve, the fluid conduit having a fluid conduit line resistor in selective fluid communication with atmosphere;
   f. an exhalation fluid line connected to the second normally-open cartridge valve, the exhalation fluid line having a first one-way valve and an expiratory resistor, the expiratory resistor in selective fluid communication with atmosphere, the first one-way valve intermediate the second normally-open cartridge and the expiratory resistor and oriented to allow fluid flow toward the expiratory resistor;
   g. an inhalation fluid line connected to the fluid conduit and to the exhalation fluid line intermediate the second normally-open cartridge valve and the first one-way valve, the inhalation fluid line having a second one-way valve and an inhalation resistor, the inhalation resistor in selective fluid communication with the exhalation fluid line, the second one-way valve intermediate the fluid conduit and the inhalation resistor and oriented to allow fluid flow toward the inhalation resistor; and
   h. a back-pressure conduit connected to the inhalation fluid line intermediate the second one-way valve and the inhalation resistor and connected to the exhalation fluid line intermediate the first one-way valve and the exhalation resistor.

10. The respiratory system of claim 9, wherein the mandatory breath support ventilation subsystem is switchable from a first position, in which gas from the pressurized gas source is supplied to the inhalation conduit upon demand for the predetermined expiratory time interval, to a second position, in which the reference chamber of the pressure regulator is vented to atmosphere through the outlet port of the normally-closed cartridge valve and gas from the pressurized gas source is supplied to the inhalation conduit for the predetermined inspiratory time interval.

11. The respiratory system of claim 10, wherein, in the first position, the first normally-open cartridge valve is open so that a distal end of the tracheal pressure conduit is in fluid communication with the reference chamber of the pressure regulator, the second normally-open cartridge valve is closed so that the mandatory breath ventilation subsystem source of pressurized gas is not in fluid communication with the fluid conduit, and the normally-closed cartridge valve is closed so that the reference chamber of the pressure regulator is not in fluid communication with atmosphere, and wherein, in the second position, the first normally-open cartridge valve is closed so that the distal end of the tracheal pressure conduit is not in fluid communication with the reference chamber of the pressure regulator, the second normally-open cartridge valve is opened so that the mandatory breath ventilation subsystem source of pressurized gas is in fluid communication with the fluid conduit, and the normally-closed cartridge valve is opened so that the reference chamber of the pressure regulator is in fluid communication with atmosphere.

12. The respiratory system of claim 9, wherein the inhalation resistor and the exhalation resistor are adjustable so that the predetermined inspiratory time interval and the predetermined expiratory time interval are selectable.

13. A respiratory system comprising:
   a. an endotracheal tube having a proximal end and a distal end;
   b. a tracheal pressure conduit in fluid communication with the distal end of the endotracheal tube;
   c. an inhalation conduit in fluid communication with the proximal end of the endotracheal tube;
   d. an exhalation conduit having an exhalation valve, the exhalation conduit in fluid communication with the proximal end of the endotracheal tube;
   e. a pressurized gas source;
   f. a demand valve in selective fluid communication with the pressurized gas source and the inhalation conduit, the demand valve movable between a first position, in which the demand valve is opened so that the inhalation conduit is in fluid communication with the pressurized gas source, and a second position, in which the demand valve is closed so that the inhalation conduit is not in fluid communication with the pressurized gas source; and,
   g. means for proportionally opening the demand valve in response to pressure within a reference chamber which is in fluid communication with the tracheal pressure conduit.

14. The respiratory system of claim 13, wherein the means for proportionally opening the demand valve opens and closes the demand valve in proportion to a baseline pressure so that the demand valve opens proportionally upon a pressure drop in the reference chamber relative to the baseline pressure and closes when pressure in the reference chamber is equal to or greater than the baseline pressure.

15. The respiratory system of claim 13, wherein the inhalation conduit further comprises a gas reservoir and a venturi tube having an inlet, an outlet, and an augmentation valve, the inlet of the venturi tube in fluid communication with the demand valve and the outlet of the venturi tube in fluid communication with the proximal end of the endotracheal tube, wherein the augmentation valve is in fluid communication with the gas reservoir.

16. The respiratory system of claim 15, wherein the augmentation valve is movable between a closed position during exhalation, in which the venturi tube is not in fluid communication with the gas reservoir, and an open position during inhalation, in which the venturi tube is in fluid communication with the gas reservoir.

17. The respiratory system of claim 15, wherein the exhalation valve has an exhalation valve control conduit in communication with the inhalation conduit intermediate the inlet of the venturi tube and the demand valve, the exhalation valve responsive to pressure in the exhalation valve control conduit so that the exhalation valve opens in proportion to a pressure drop in the exhalation valve control conduit relative to pressure in the exhalation conduit and is closed when pressure in the exhalation valve control conduit is equal to or greater than pressure in the exhalation conduit.

18. The respiratory system of claim 17, wherein the exhalation valve control conduit has a selectable restrictor valve movable from an open position, in which fluid flow through the exhalation valve control conduit is unrestricted, towards a closed position, in which fluid flow through the exhalation valve control conduit is restricted so that, when the exhalation valve control conduit is restricted, resistance of the exhalation valve to open is lowered.

19. The respiratory system of claim 13, wherein the demand valve is adjustable so that the baseline pressure is selectable.

20. The respiratory system of claim 13, further comprising a pressure sensor having an indicator to display pressure, the pressure sensor in operative communication with the tracheal pressure conduit so that pressure within the tracheal pressure conduit may be displayed.

21. The respiratory system of claim 13, wherein the opening means includes a spring operatively connected to the demand valve for opening the demand valve.

22. The respiratory system of claim 13, further comprising a mandatory breath support ventilation subsystem to supply gas from the pressurized gas source to the inhalation conduit at a predetermined inspiratory time interval and a predetermined expiratory time interval.

23. The respiratory system of claim 22, wherein the mandatory breath ventilation subsystem comprises:
   a. a mandatory breath ventilation subsystem source of pressurized gas;
   b. a first normally-open cartridge valve connected to the tracheal pressure conduit;
   c. a second normally-open cartridge valve connected to the mandatory breath ventilation subsystem source of pressurized gas;
   d. a normally-closed cartridge valve connected to the tracheal pressure conduit intermediate the first normally-open cartridge valve and the reference chamber of the pressure regulator, the normally-closed cartridge valve having an outlet port in selective fluid communication with atmosphere;
   e. a fluid conduit connected to the first normally-open cartridge valve, the second normally-open cartridge valve, and the normally-closed cartridge valve, the fluid conduit having a fluid conduit line resistor in selective fluid communication with atmosphere;

f. an exhalation fluid line connected to the second normally-open cartridge valve, the exhalation fluid line having a first one-way valve and an expiratory resistor, the expiratory resistor in selective fluid communication with atmosphere, the first one-way valve intermediate the second normally-open cartridge and the expiratory resistor and oriented to allow fluid flow toward the expiratory resistor;

g. an inhalation fluid line connected to the fluid conduit and to the exhalation fluid line intermediate the second normally-open cartridge valve and the first one-way valve, the inhalation fluid line having a second one-way valve and an inhalation resistor, the inhalation resistor in selective fluid communication with the exhalation fluid line, the second one-way valve intermediate the fluid conduit and the inhalation resistor and oriented to allow fluid flow toward the inhalation resistor; and h. a back-pressure conduit connected to the inhalation fluid line intermediate the second one-way valve and the inhalation resistor and connected to the exhalation fluid line intermediate the first one-way valve and the exhalation resistor.

24. The respiratory system of claim 23, wherein the mandatory breath support ventilation subsystem is switchable from a first position, in which gas from the pressurized gas source is supplied to the inhalation conduit upon demand for the predetermined expiratory time interval, to a second position, in which the reference chamber is vented to atmosphere through the outlet port of the normally-closed cartridge valve and gas from the pressurized gas source is supplied to the inhalation conduit for the predetermined inspiratory time interval.

25. The respiratory system of claim 24, wherein, in the first position, the first normally-open cartridge valve is open so that a distal end of the tracheal pressure conduit is in fluid communication with the reference chamber, the second normally-open cartridge valve is closed so that the mandatory breath ventilation subsystem source of pressurized gas is not in fluid communication with the fluid conduit, and the normally-closed cartridge valve is closed so that the reference chamber is not in fluid communication with atmosphere, and wherein, in the second position, the first normally-open cartridge valve is closed so that the distal end of the tracheal pressure conduit is not in fluid communication with the reference chamber, the second normally-open cartridge valve is opened so that the mandatory breath ventilation subsystem source of pressurized gas is in fluid communication with the fluid conduit and the normally-closed cartridge valve is opened so that the reference chamber is in fluid communication with atmosphere.

26. The respiratory system of claim 23, wherein the inhalation resistor and the exhalation resistor are adjustable so that the predetermined inspiratory time interval and the predetermined expiratory time interval are selectable.

27. A respiratory system comprising:

a. an endotracheal tube having a proximal end and a distal end;

b. a tracheal pressure conduit in fluid communication with the distal end of the endotracheal tube;

c. an inhalation conduit having a venturi tube and a gas reservoir, the inhalation conduit in fluid communication with the proximal end of the endotracheal tube, the venturi tube having an augmentation valve in fluid communication with the gas reservoir;

d. an exhalation conduit including an exhalation valve, the exhalation conduit in fluid communication with the proximal end of the endotracheal tube;

e. a pressurized gas source; and f. a pressure regulator having a reference chamber and a demand valve in selective fluid communication with the pressurized gas source with the inhalation conduit, wherein the reference chamber is in fluid communication with the tracheal pressure conduit, wherein the demand valve is responsive to pressure within the reference chamber to open and close in proportion to a baseline pressure, wherein the demand valve is proportionally moveable between a first position during inhalation, in which the demand valve is opened so that the inhalation conduit is in fluid communication with the pressurized gas source, and a second position during exhalation, in which the demand valve is closed so that the inhalation conduit is not in fluid communication with the pressurized gas source, and wherein the demand valve opens proportionally upon a pressure drop in the reference chamber relative to the baseline pressure and is closed when pressure in the reference chamber is equal to or greater than the baseline pressure.

28. The respiratory system of claim 27, wherein the venturi tube further includes an inlet and an outlet, the inlet of the venturi tube in communication with the demand valve and the outlet of the venturi tube in communication with the proximal end of the endotracheal tube.

29. The respiratory system of claim 27, wherein the augmentation valve is movable between a closed position during exhalation, in which the venturi tube is not in fluid communication with the gas reservoir, and an opened position during inhalation, in which the venturi tube is in fluid communication with the gas reservoir.

30. The respiratory system of claim 28, wherein the exhalation valve of the exhalation conduit has an exhalation valve control conduit in fluid communication with the inhalation conduit intermediate the inlet of the venturi tube and the demand valve of the pressure regulator, the exhalation valve responsive to pressure in the exhalation valve control conduit so that the exhalation valve opens in proportion to a pressure drop in the exhalation valve control conduit relative to pressure in the exhalation conduit and is closed when pressure in the exhalation valve control conduit is equal to or greater than pressure in the exhalation conduit.

31. The respiratory system of claim 30, wherein the exhalation valve control conduit has a selectable restrictor valve movable from an open position, in which fluid flow through the exhalation valve control conduit is unrestricted, towards a closed position, in which fluid flow through the exhalation valve control conduit is restricted so that, when the exhalation valve control conduit is restricted, resistance of the exhalation valve to open is lowered.

32. The respiratory system of claim 27, wherein the demand valve of the pressure regulator is adjustable so that the baseline pressure is selectable.

33. The respiratory system of claim 27, further comprising a pressure sensor having an indicator to display pressure, the pressure sensor in fluid communication with the tracheal pressure conduit so that pressure within the tracheal pressure conduit may be displayed.

34. The respiratory system of claim 27, further comprising a mandatory breath support ventilation subsystem to supply gas from the pressurized gas source to the inhalation conduit at a predetermined inspiratory time interval and a predetermined expiratory time interval.

35. The respiratory system of claim 34, wherein the mandatory breath ventilation subsystem comprises:

a. a mandatory breath ventilation subsystem source of pressurized gas;
   b. a first normally-open cartridge valve connected to the tracheal pressure conduit;
   c. a second normally-open cartridge valve connected to the mandatory breath ventilation subsystem source of pressurized gas;
   d. a normally-closed cartridge valve connected to the tracheal pressure conduit intermediate the first normally-open cartridge valve and the reference chamber of the pressure regulator, the normally-closed cartridge valve having an outlet port in selective fluid communication with atmosphere;
   e. a fluid conduit connected to the first normally-open cartridge valve, the second normally-open cartridge valve, and the normally-closed cartridge valve, the fluid conduit having a fluid conduit line resistor in selective fluid communication with atmosphere;
   f. an exhalation fluid line connected to the second normally-open cartridge valve, the exhalation fluid line having a first one-way valve and an expiratory resistor, the expiratory resistor in selective fluid communication with atmosphere, the first one-way valve intermediate the second normally-open cartridge and the expiratory resistor and oriented to allow fluid flow toward the expiratory resistor;
   g. an inhalation fluid line connected to the fluid conduit and to the exhalation fluid line intermediate the second normally-open cartridge valve and the first one-way valve, the inhalation fluid line having a second one-way valve and an inhalation resistor, the inhalation resistor in selective fluid communication with the exhalation fluid line, the second one-way valve intermediate the fluid conduit and the inhalation resistor and oriented to allow fluid flow toward the inhalation resistor; and,
   h. a back-pressure conduit connected to the inhalation fluid line intermediate the second one-way valve and the inhalation resistor and connected to the exhalation fluid line intermediate the first one-way valve and the exhalation resistor.

36. The respiratory system of claim 35, wherein the mandatory breath support ventilation subsystem is switchable from a first position, in which gas from the pressurized gas source is supplied to the inhalation conduit upon demand for the predetermined expiratory time interval, to a second position, in which the reference chamber of the pressure regulator is vented to atmosphere through the outlet port of the normally-closed cartridge valve and gas from the pressurized gas source is supplied to the inhalation conduit for the predetermined inspiratory time interval.

37. The respiratory system of claim 36, wherein, in the first position, the first normally-open cartridge valve is open so that a distal end of the tracheal pressure conduit is in fluid communication with the reference chamber of the pressure regulator, the second normally-open cartridge valve is closed so that the mandatory breath ventilation subsystem source of pressurized gas is not in fluid communication with the fluid conduit, and the normally-closed cartridge valve is closed so that the reference chamber of the pressure regulator is not in fluid communication with atmosphere, and wherein, in the second position, the first normally-open cartridge valve is closed so that the distal end of the tracheal pressure conduit is not in fluid communication with the reference chamber of the pressure regulator, the second normally-open cartridge valve is opened so that the mandatory breath ventilation subsystem source of pressurized gas is in fluid communication with the fluid conduit, and the normally-closed cartridge valve is opened so that the reference chamber of the pressure regulator is in fluid communication with atmosphere.

38. The respiratory system of claim 35, wherein the inhalation resistor and the exhalation resistor are adjustable so that the predetermined inspiratory time interval and the predetermined expiratory time interval are selectable.

* * * * *